(12) United States Patent  
Rothschild et al.

(10) Patent No.: US 7,074,562 B2  
(45) Date of Patent: Jul. 11, 2006

(54) GHRELIN ALLELES AND USE OF THE SAME FOR GENETICALLY TYPING ANIMALS

(75) Inventors: Max F. Rothschild, Ames, IA (US); Kwan-Suk Kim, Ames, IA (US); Lloyd L. Anderson, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 375 days.

(21) Appl. No.: 10/294,191

(22) Filed: Nov. 14, 2002

(65) Prior Publication Data

US 2003/0211512 A1     Nov. 13, 2003

Related U.S. Application Data

(60) Provisional application No. 60/333,222, filed on Nov. 14, 2001.

(51) Int. Cl.
*C12Q 1/68* (2006.01)
*C12P 19/34* (2006.01)

(52) U.S. Cl. .......................................... 435/6; 435/91.2
(58) Field of Classification Search ................... 435/6; 536/23.1

See application file for complete search history.

(56) References Cited

OTHER PUBLICATIONS

Skibola et al. "Polymorphisms in Ghrelin and Neuropeptide Y Genes are Associated with Non-Hodgkin Lymphoma." Cancer Epidemiology Biomarkers Prevention. May 2005, 14(5). pp. 1251-1256.*
Thisted, R. "What is a P-value" (1998) Http://www.stat.uchicago.edu/ Thisted.*

* cited by examiner

*Primary Examiner*—Gary Benzion
*Assistant Examiner*—Christopher M. Babic
(74) *Attorney, Agent, or Firm*—McKee, Voorhees & Sease, P.L.C.

(57) ABSTRACT

Disclosed herein are genetic markers for animal growth, appetite and fatness, methods for identifying such markers, and methods of screening animals to determine those more likely to produce desired growth, appetite and fatness and preferably selecting those animals for future breeding purposes. The markers are based upon the presence or absence of certain polymorphisms in the Ghrelin gene.

6 Claims, 9 Drawing Sheets

|          |                                                                                      |               |
|----------|--------------------------------------------------------------------------------------|---------------|
| Mouse    | MLSSGTICSLLLLSMIWM-DMAMAGSSFLSPEHQKAQQRKESKKPPAKLQPRALEGWLHPE                         | SEQ ID NO:1   |
| Bovine   | MPAPWTICSLLLLSVLCM-DLAMAGSSFLSPEHQKLQ-RKEAKKPSGRLKPRTLEGQFDPE                         | SEQ ID NO:2   |
| Human    | MPSPGTVCSLLLLGMIWL-DLAMAGSSFLSPEHQRVQQRKESKKPPAKLQPRALAGWLRPE                         | SEQ ID NO:3   |
| Porcine  | MPSTGTICSLLLLSVLLMADIAMAGSSFLSPEHQKVQQRKESKKPAAKLKPRALEGWLGPE                         | SEQ ID NO:4   |
| *        | MPSTGTICSLLLLSVLLMADIAMAGSSFLSPEHQKVQQRKESKKPAAKLKPRALEGWLGPE                         | SEQ ID NO:5   |

|          |                                                                                      |               |
|----------|--------------------------------------------------------------------------------------|---------------|
| Mouse    | DRGQAETEEELEIRFNAPFDVGIKLSGAQYQQHGRALGKFLQDILWEEVKEAPADK                              | SEQ ID NO:6   |
| Bovine   | VGSQAEDELEIRFNAPFNIGIKLAGAQSLQHGQTLGKFLQDILWEEAETLANE                                 | SEQ ID NO:7   |
| Human    | DGGQAEDELEVRFNAPFDVGIKLSGVQYQQHSQALGKFLQDILWEEAKEAPADK                                | SEQ ID NO:8   |
| Porcine  | DSGEVEGTEDKLEIRFNAPCDVGIKLSGAQSDQHGQPLGKFLQDILWEEVTEAPADK                             | SEQ ID NO:9   |
| *        | DSGEVEGTEDNLEIRFNAPCDVGIKLSGAQSDQHGQPLGKFLQDILWEEVNEAPADK                             | SEQ ID NO:10  |

*Fig.1*

Start codon
AGCTGAGGCCATGCCCTCCACGGGGACCATTTGCAGCCTGCTGCTCCTCAGCGTGCTCCTCAT

GGCAGACTTGGCCATGGCGGGCTCCAGCTTCTTGAGCCCCGAACACCAGAAAGTGCAGGTAA

GACGTCTCCCCAGAGCCCCGGCTTCTGGCGGGTACCTCATCCCAGCCCTTCCATGAGTTGGGA
                  A

CCTGGGCTCACCTGCTCTGGGCTTCAGGCCTCTCCCAAGGAGGACTCTGGATCTGCAAGGGAG
                                                              G

CCCATACCTTGCTCTGCTTCTGGAAGGAAGTAGTGGGGGTGGGTGGGCATCTTAGGGCCTC

AAGAGAGCAGTTCCTCTTTCCAGCAGAGAAAGGAGTCCAAGAAGCCAGCAGCCAAACTGAA

GCCCCGGGCCCTGGAAGGCTGGCTCGGCCCAGAAGACAGTGGTGAGGTGGAAGGCACGG

AGGACAAGCTGGAAA    SEQ ID NO: 11
        T

*Fig 3*

```
TCAGTCCGACCAGCACGGCCAGCCCCTGGGGAAATTTCTCCAGGACATCCTCTGGGAA

GAGGTCAATGGTAAGTCCCCGTCCCGGCTAAGGTCAATTCCAAGTTCCTGGGAGTCCCA
         C

GTGTGAGCCCATCTATGGGTAACAAAACAGAAATTTCCTTCCCCATCCCTGCCTCTCTAA

AGAGCTTCTGTGGCCTTCTGTGGCACAGGATCCAATGTTGTTACTATAGAGTTTTGGGTC
                                 G                G      A

ACTGCAGTGGTGTGGGCCTGGGAAGTTCCACATGCTGCAAGTACAGCCAAAAAATAAAA
                                         G

AAGGGCCTTTAATTGCTCTTTCCCGGGAGTTCCCGTTGTGGCTCAGCAGTTAGCGAATCT
                 C

GACTAGCATCCATGAGGATGCAGGTTCGATCCCTGGCCTTACTCAGTGGGTTAAAGATC
                                                       G

TGGCATTGCCGTGAACTGTGGTGTAGTTGCAGACACGGCTCAGATCCTGCATTGCTGTG
                                    G       A

TCTGTGGTGTAGGCCGGTAGCTACAGCTCCGATTTGACCCCTAACCTGGGAACCTNCTT

ATGCTGCAAGTGCTGCCCTGAAAAAGAAAAAAAAAAACTGNNNNNNNNNNNNNNNNNNN
NNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNTTTTTTTTTTTTTTCCCCTTTTTTTTT

TTTTTTTTTGGCCATGCGTGCAGCATGCCAATGTTCCTAGGCCAGGGAACCCAAGCCAC

AGCAGTGACAACCCTGGATCCTTAAGGAACTAGGCCACCAGGGAACTCCAGAAAAGCCA

TCTCTGATGGCAATGGCAGAACAGCACAGAATTTTGACTTGATCTCTTGCTTTTCAGAGG
              C

CCCCGGCCGACAAGTGATTGTCCCTGAGACCAGCCACCTCTGTTCTCCCAGCCTCCTAA
    Stop codon                                       T

GGGCTCACNTGGCTTACAGTACGCTTCC   SEQ ID NO: 12
```

*Fig. 4*

GHRELIN ALLELES AND USE OF THE SAME FOR GENETICALLY TYPING ANIMALS

CROSS-REFERENCE TO RELATED APPLICATIONS

This application claims benefit under 35 U.S.C. § 119(e) of provisional application No. 60/333,222, filed Nov. 14, 2001, the disclosure of which is hereby incorporated by reference in its entirety.

GRANT REFERENCE

This invention was supported at least in part by USDA/CREES contract number 2001-31200-06019 (IHAEES project number IOWO3600). The United States government may have certain rights in this invention.

BACKGROUND OF THE INVENTION

Genetic differences exist among individual animals as well as among breeds which can be exploited by breeding techniques to achieve animals with desirable characteristics. For example, Chinese breeds are known for reaching puberty at an early age and for their large litter size, while American breeds are known for their greater growth rates and leanness. However, heritability for desired traits is often low, and standard breeding methods which select individuals based upon phenotypic variations do not take fully into account genetic variability or complex gene interactions which exist.

Restriction fragment length polymorphism (RFLP) analysis has been used by several groups to study pig DNA. Jung et al., *Theor. Appl. Genet.*, 77:271–274 (1989), incorporated herein by reference, discloses the use of RFLP techniques to show genetic variability between two pig breeds. Polymorphism was demonstrated for swine leukocyte antigen (SLA) Class I genes in these breeds. Hoganson et al., *Abstract for Annual Meeting of Midwestern Section of the American Society of Animal Science*, Mar. 26–28, 1990, incorporated herein by reference, reports on the polymorphism of swine major histocompatibility complex (MHC) genes for Chinese pigs, also demonstrated by RFLP analysis. Jung et al., *Theor. Appl. Genet.*, 77:271–274 (1989), incorporated herein by reference, reports on RFLP analysis of SLA Class I genes in certain boars. The authors state that the results suggest that there may be an association between swine SLA/MHC Class I genes and production and performance traits. They further state that the use of SLA Class I restriction fragments, as genetic markers, may have potential in the future for improving pig growth performance.

The ability to follow a specific favorable genetic allele involves a novel and lengthy process of the identification of a DNA molecular marker for a major effect gene. The marker may be linked to a single gene with a major effect or linked to a number of genes with additive effects. DNA markers have several advantages; segregation is easy to measure and is unambiguous, and DNA markers are co-dominant, i.e., heterozygous and homozygous animals can be distinctively identified. Once a marker system is established selection decisions could be made very easily, since DNA markers can be assayed any time after a tissue or blood sample can be collected from the individual infant animal, or even an embryo.

The use of genetic differences in receptor genes has become a valuable marker system for selection. For example, U.S. Pat. Nos. 5,550,024 and 5,374,526 issued to Rothschild et al. disclose a polymorphism in the pig estrogen receptor gene which is associated with larger litter size, the disclosure of which is incorporated herein by reference. U.S. Pat. No. 5,935,784 discloses polymorphic markers in the pig prolactin receptor gene which are associated with larger litter size and overall reproductive efficiency.

Litter size, of course has a direct economic impact for a breeder. Also important for meat producing animals is growth, appetite and fatness.

The quality of raw pig meat is influenced by a large number of genetic and non-genetic factors. The latter include farm, transport, slaughter and processing conditions. Meat scientists have performed a substantial amount of research on these factors, which has led to considerable quality improvement. Part of the research has also been dedicated to the genetic background of the animals, and several studies have revealed the importance of genetic factors. This has made the industry aware that selective breeding of animals and the use of gene technology can play an important role in enhancing pork quality.

Information at the DNA level can not only help to fix a specific major gene, but it can also assist the selection of quantitative traits for which we already select. Molecular information in addition to phenotypic data can increase the accuracy of selection and therefore the selection response. The size of the extra response in such a Marker Assisted Selection (MAS) program has been considered by many workers from a theoretical point of view. In general terms, MAS is more beneficial for traits with a low heritability and which are expensive to measure phenotypically. Although traits such as growth, appetite and fatness are not typically considered in this way, there are still significant advantages for the use of markers for these traits. For example, Meuwissen and Goddard considered the impact of MAS for different types of traits. The biggest impacts were for traits such as meat quality, where the trait is measured after slaughter and an additional response of up to 64% could be achieved with the incorporation of marker information. This figure was relatively small, 8%, for growth traits that can be measured on the live animal. However, once the association has been demonstrated this marker information can be used before the animals are tested or selected phenotypically (see below) and in this situation a response of up to 38% was predicted.

Indeed, the best approach to genetically improve economic traits is to find relevant DNA-markers directly in the population under selection. Phenotypic measurements can be performed continuously on some animals from the nucleus populations of breeding organizations. Since a full assessment of most of these traits can only be done after slaughter, the data must be collected on culled animals and cannot be obtained on potential breeding animals.

This phenotypic data is collected in order to enable the detection of relevant DNA markers, and to validate markers identified using experimental populations or to test candidate genes. Significant markers or genes can then be included directly in the selection process. An advantage of the molecular information is that we can obtain it at a very young age in the breeding animal, which means that animals can be preselected based on DNA markers before the growing performance test is completed. This is a great advantage for the overall testing and selection system.

It can be seen from the foregoing that a need exists for identification of markers which may be used to improve economically beneficial characteristics in animals by identifying and selecting animals with the improved characteristics at the genetic level.

An object of the present invention is to provide a genetic marker based on or within the Ghrelin gene which is indicative of favorable economic characteristics such as growth, appetite and fatness.

Another object of the invention is to provide an assay for determining the presence of this genetic marker.

A further object of the invention is to provide a method of evaluating animals that increases accuracy of selection and breeding methods for the desired traits.

Yet another object of the invention is to provide a PCR amplification test which will greatly expedite the determination of presence of the marker.

Additional objects and advantages of the invention will be set forth in part in the description that follows, and in part will be obvious from the description, or may be learned by the practice of the invention. The objects and advantages of the invention will be attained by means of the instrumentalities and combinations particularly pointed out in the appended claims.

BRIEF SUMMARY OF THE INVENTION

This invention relates to the discovery of alternate gene forms of the Ghrelin gene which are useful as genetic markers associated with growth, appetite and fatness traits in animals. To the extent that these genes are conserved among species and animals, it is expected that the different alleles disclosed herein will also correlate with variability in this gene in other economic or meat-producing animals such as bovine, sheep, chicken, etc.

To achieve the objects and in accordance with the purpose of the invention, as embodied and broadly described herein, the present invention provides the discovery of alternate genotypes which provide a method for screening animals to determine those more likely to possess favorable growth, appetite and fatness traits or to select against pigs which have alleles indicating less favorable growth, appetite and fatness traits. As used herein "favorable growth, appetite and fatness trait" means a significant improvement (increase or decrease) in one of many measurable growth, appetite and fatness traits above the mean of a given population, so that this information can be used in breeding to achieve a uniform population which is optimized for growth, appetite and fatness, this may include an increase in some traits or a decrease in others depending on the desired characteristics. For a review of economic traits the following may be consulted: Sosnicki, A. A., E. R. Wilson, E. B. Sheiss, A. deVries, 1998, "Is there a cost effective way to produce high quality pork?", *Reciprocal Meat Conference Proceedings*, Vol. 51.

Thus, the present invention provides a method for screening pigs to identify those more likely to produce favorable growth, appetite and fatness, and/or those less likely to produce favorable growth, appetite and fatness to optimize breeding and selection techniques for the best growth, appetite and fatness.

Methods for assaying for these traits generally comprises the steps 1) obtaining a biological sample from a pig; and 2) analyzing the genomic DNA or protein obtained in 1) to determine which Ghrelin allele(s) is/are present. Also included herein are haplotype data which allows for a series of polymorphisms in the Ghrelin gene to be combined in a selection or identification protocol to maximize the benefits of each of these markers.

Since several of the polymorphisms involve changes in amino acid composition of the Ghrelin protein, assay methods may even involve ascertaining the amino acid composition of the Ghrelin protein. Methods for this type or purification and analysis typically involve isolation of the protein through means including fluorescence tagging with antibodies, separation and purification of the protein (i.e., through reverse phase HPLC system), and use of an automated protein sequencer to identify the amino acid sequence present. Protocols for this assay are standard and known in the art and are disclosed in Ausubel et. al.(eds.), *Short Protocols in Molecular Biology* (4th ed. John Wiley and Sons 1999).

In a preferred embodiment, a genetic sample is analyzed. Briefly, a sample of genetic material is obtained from an animal, and the sample is analyzed to determine the presence or absence of a polymorphism in the Ghrelin gene that is correlated with improved growth, appetite and fatness or both traits depending on the gene form.

As is well known to those of skill in the art, a variety of techniques may be utilized when comparing nucleic acid molecules for sequence differences. These include by way of example, restriction fragment length polymorphism analysis, heteroduplex analysis, single strand conformation polymorphism analysis, denaturing gradient electrophoresis and temperature gradient electrophoresis.

In a preferred embodiment, the polymorphism is a restriction fragment length polymorphism and the assay comprises identifying the pig Ghrelin gene from isolated genetic material; exposing the gene to a restriction enzyme that yields restriction fragments of the gene of varying length; separating the restriction fragments to form a restriction pattern, such as by electrophoresis or HPLC separation; and comparing the resulting restriction fragment pattern from a Ghrelin gene that is either known to have or not to have the desired marker. If an animal tests positive for the markers, such animal can be considered for inclusion in the breeding program. If the animal does not test positive for the marker genotype the animal can be culled from the group and otherwise used. Use of haplotype data can also be incorporated with the screening for multiple alleles for different aspects of growth, appetite and fatness.

In a most preferred embodiment, the gene is isolated by the use of primers and DNA polymerase to amplify a specific region of the gene which contains the polymorphism. Next the amplified region is digested with a restriction enzyme and fragments are again separated. Visualization of the RFLP pattern is by simple staining of the fragments, or by labeling the primers or the nucleoside triphosphates used in amplification.

In another embodiment, the invention comprises a method for identifying a genetic marker for growth, appetite and fatness in a particular population. Male and female pigs of the same breed or breed cross or similar genetic lineage are bred, and growth, appetite and fatness produced by each pig is determined. A polymorphism in the Ghrelin gene of each pig is identified and associated with the growth, appetite and fatness. Preferably, RFLP analysis is used to determine the polymorphism (FIGS. 2A–H).

In another embodiment, the invention comprises a method for identifying a genetic marker for growth, appetite and fatness in any particular economic animal other than a pig. Based upon the highly conserved nature of this gene among different animals, it is expected that with no more than routine testing as described herein, this marker can be applied to different animal species to select for growth, appetite and fatness based on the teachings herein. Male and female animals of the same breed or breed cross or similar genetic lineage are bred, and the growth, appetite and fatness produced by each animal is determined and correlated. For other animals in which sequences are available a BLAST comparison of sequences may be used to ascertain whether the particular allele is analogous to the one disclosed herein. The analogous polymorphism will be present in other animals and in other closely related genes. The term "analogous polymorphism" shall be a polymorphism which is the same as any of those disclosed herein as determined by BLAST comparisons.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. In this case the reference is the Ghrelin sequence. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237–244 (1988); Higgins and Sharp, *CABIOS* 5:151–153 (1989); Corpet, et al., *Nucleic Acids Research* 16:10881–90 (1988); Huang, et al., *Computer Applications in the Biosciences* 8:155–65 (1992), and Pearson, et al., *Methods in Molecular Biology* 24:307–331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., *Nucleic Acids Res.* 25:3389–3402 (1997). Software for performing BLAST analyses is publicly available, e.g., through the National Center for Biotechnology-Information http:// worldwide web at hcbi.nlm.nih. gov.

This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Natl. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149–163 (1993)) and XNU (Claverie and States, *Comput. Chem.*, 17:191–201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.,* 4:11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or preferably at least 70%, 80%, 90%, and most preferably at least 95%.

These programs and algorithms can ascertain the analogy of a particular polymorphism in a target gene to those disclosed herein. It is expected that this polymorphism will exist in other animals and be of use in other animals than disclosed herein involved no more than routine optimization of parameters using the teachings herein.

It is also possible to establish linkage between specific alleles of alternative DNA markers and alleles of DNA markers known to be associated with a particular gene (e.g., the Ghrelin gene discussed herein), which have previously been shown to be associated with a particular trait. Thus, in the present situation, taking the Ghrelin gene, it would be possible, at least in the short term, to select for pigs likely to produce desired growth, appetite and fatness, or alternatively against pigs likely to produce less desirable growth, appetite and fatness, indirectly, by selecting for certain alleles of a Ghrelin associated marker through the selection of specific alleles of alternative chromosome markers. As used herein, the term "genetic marker" shall include not only the polymorphism disclosed by any means of assaying for the protein changes associated with the polymorphism, be they linked markers, use of microsatellites, or even other means of assaying for the causative protein changes indicated by the marker, and the use of the marker to influence the growth, appetite and fatness of an animal.

As used herein, often the designation of a particular polymorphism is made by the name of a particular restriction enzyme. This is not intended to imply that the only way that the site can be identified is by the use of that restriction enzyme. There are numerous databases and resources available to those of skill in the art to identify other restriction enzymes which can be used to identify a particular polymorphism, for example http://world wide web at darwin.bio.geneseso.edu which can give restriction enzymes upon analysis of a sequence and the polymorphism to be identified. In fact, as disclosed in the teachings herein, there are numerous ways of identifying a particular polymorphism or allele with alternate methods which may not even include a restriction enzyme, but which assay for the same genetic or proteomic alternative form.

As used herein, "polymorphism" refers to DNA sequence variation in the cellular genomes of plants or animals, preferably mammals. These sequence variations include mutations, single nucleotide changes and insertions and deletions. "Single nucleotide polymorphism" (SNP) refers to those differences among samples of DNA in which a single nucleotide base pair has been substituted by another.

As used herein, "phenotype" refers to any observable or otherwise measurable physiological, morphological, biological, biochemical or clinical characteristic of an organism.

As used herein, "genotype" refers to the genetic constitution of an organism. More specifically, "genotyping" as used herein refers to the analysis of DNA in a sample obtained from a subject to determine the DNA sequence in a specific region of the genome—e.g. at a gene that influences a trait. The term "genotyping" may refer to the determination of DNA sequence at one or more polymorphic sites.

As used herein, "haplotype" refers to the partial or complete sequence of a segment of DNA from a single chromosome. The DNA segment may include part of a gene, an entire gene, several genes, or a region devoid of genes (but which perhaps contains a DNA sequence that regulates the function of nearby genes). The haplotype preserves information about the phase of the polymorphic nucleotides—that is, which set of variances were inherited from one parent (and are therefore on one chromosome), and which from the other. Haplotypes are generally inherited as units, except in the event of a recombination during meiosis that occurs within the DNA segment spanned by the haplotype—a rare occurrence for any given sequence in each generation.

The term "associated with" in connection with the relationship between a genetic characteristic, e.g., a gene, allele, haplotype, or polymorphism, and a trait means that there is a statistically significant level of relatedness between them based on any generally accepted statistical measure of relatedness. Those skilled in the art are familiar with selecting an appropriate statistical measure for a particular experimental situation or data set.

The accompanying figures, which are incorporated herein and which constitute a part of this specification, illustrate one embodiment of the invention and, together with the description, serve to explain the principles of the invention.

BRIEF DESCRIPTION OF THE DRAWINGS

FIG. 1 shows a sequence comparison of the ghrelin protein (SEQ ID NOs: 1–10). *The porcupine ghrelin sequence contains amino acid changes, which are indicated with bold.

FIG. 3 shows the consensus sequence of the porcupine ghrelin fragment spanning exon 1 and 2 (447 bp) (SEQ ID NO: 11). The blocked regions indicate the coding region. The polymorphic site is underlined. N is not determined.

FIG. 4 is a continuation of the consensus sequence of the porcupine ghrelin fragment spanning exon 3 and 4 (1.1 kb) (SEQ ID NO: 12). The blocked regions indicate the coding region. The polymorphic site is underlined. N is not determined.

DETAILED DESCRIPTION OF THE INVENTION

Reference will now be made in detail to the presently referred embodiments of the invention, which together with the following examples, serve to explain the principles of the invention.

Ghrelin has been identified as an endogenous ligand to the growth hormone (GH) secretagogue receptor, which stimulates GH release and food intake.

Figure 5:
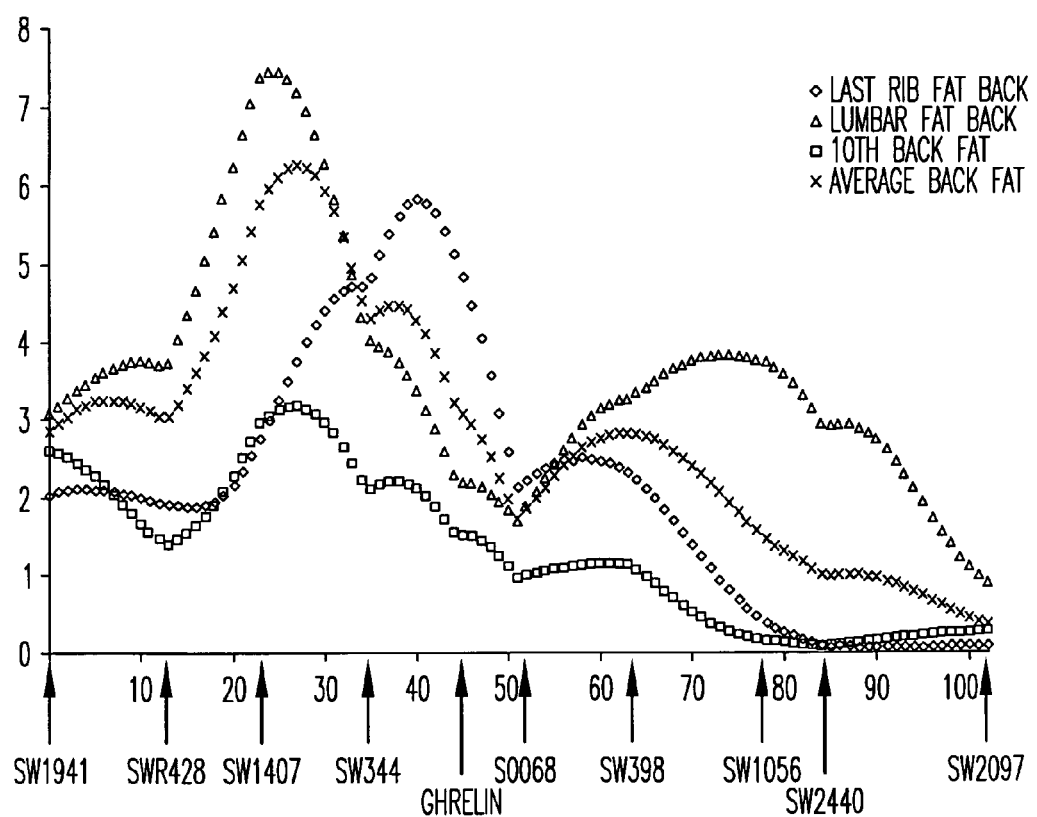
FIG. 5 shows the QTL analyses of the ghrelin in the Berkshire and Yorkshire crossed population for fatness traits on the pig chromosome 13.
Figure 6:
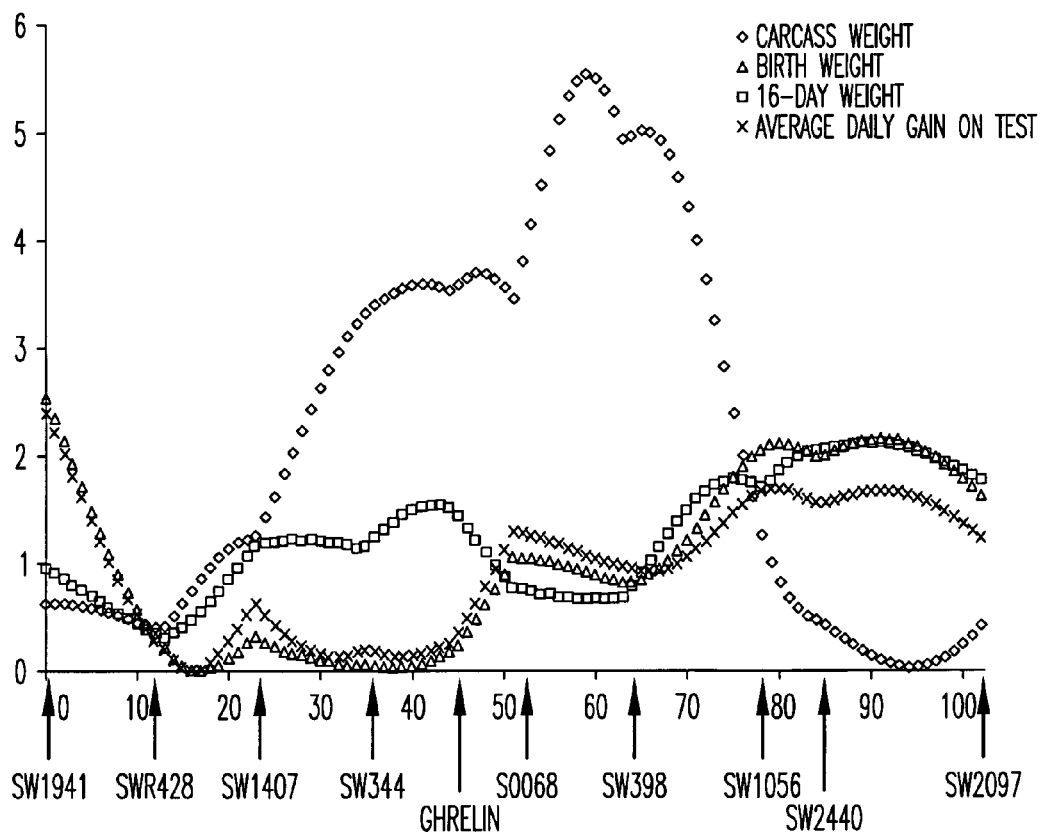
FIG. 6 shows the QTL analyses of the ghrelin in the Berkshire and Yorkshire crossed population for carcass traits on the pig chromosome 13.
Figure 7:
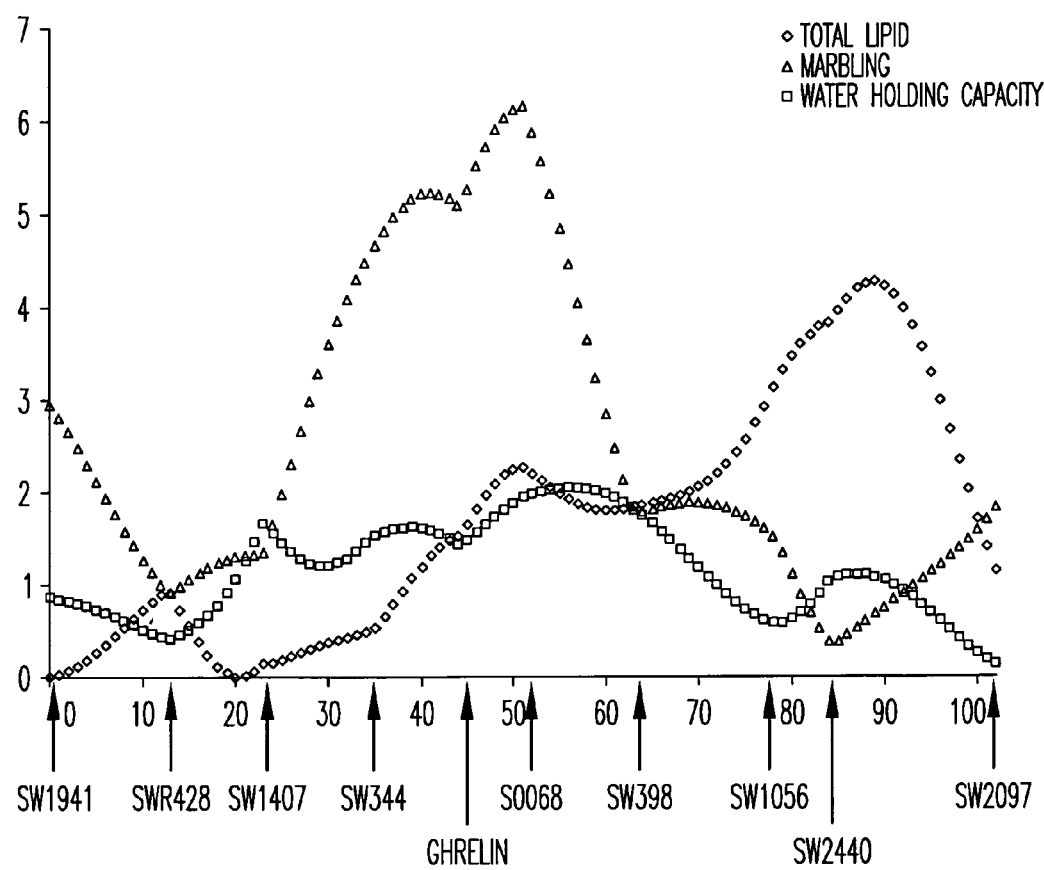
FIG. 7 shows the QTL analyses of the ghrelin in the Berkshire and Yorkshire crossed population for pork quality traits on the pig chromosome 13.

According to the invention, applicants have identified several single nucleotide polymorphisms (SNPs) in the pig ghrelin gene and these SNPs were used for linkage mapping and association between ghrelin polymorphisms and GH expression and plasma levels. Applicants have found that the ghrelin gene is linked with several markers on pig chromosome 13 of the PiGMaP, and the ISU Berkshire and Yorkshire crossed reference families and is located under QTL for fatness and meat quality traits. In the PiGMap reference family, the Ghrelin gene maps close to S0223 and S0281. This gene is therefore linked to fat and growth markers. Although GH mRNA concentration was not associated with ghrelin polymorphisms, one of the polymorphisms, Type I of the BsrI polymorphism, was significantly associated with plasma GH concentration (p<0.03). This suggests that the ghrelin gene is a good candidate for the growth and fatness Quantitative trait locus (QTL) reported on pig chromosome 13 (FIGS. 5–7).

Therefore, the invention relates to genetic markers for economically valuable traits in animals. The markers represent alleles that are associated significantly with a growth, appetite and fatness trait and thus provides a method of screening animals to determine those more likely to produce desired growth, appetite and fatness (levels of one or all of these) when bred by identifying the presence or absence of a polymorphism in the Ghrelin gene that is so correlated.

Thus, the invention relates to genetic markers and methods of identifying those markers in an animal of a particular breed, strain, population, or group, whereby the animal is more likely to yield meat of desired growth, appetite and fatness.

Any method of identifying the presence or absence of this marker may be used, including for example single-strand conformation polymorphism (SSCP) analysis, base excision sequence scanning (BESS), RFLP analysis, heteroduplex analysis, denaturing gradient gel electrophoresis, temperature gradient electrophoresis, allelic PCR, ligase chain reaction direct sequencing, mini sequencing, nucleic acid hybridization, and micro-array-type detection of the Ghrelin gene, or other linked sequences of the Ghrelin gene. Also within the scope of the invention includes assaying for protein conformational or sequences changes which occur in the presence of this polymorphism. The polymorphism may or may not be the causative mutation but will be indicative of the presence of this change and one may assay for the genetic or protein bases for the phenotypic difference.

The following is a general overview of techniques which can be used to assay for the polymorphisms of the invention.

In the present invention, a sample of genetic material is obtained from an animal. Samples can be obtained from blood, tissue, semen, etc. Generally, peripheral blood cells are used as the source, and the genetic material is DNA. A sufficient amount of cells are obtained to provide a sufficient amount of DNA for analysis. This amount will be known or readily determinable by those skilled in the art. The DNA is isolated from the blood cells by techniques known to those skilled in the art.

Isolation and Amplification of Nucleic Acid

Samples of genomic DNA are isolated from any convenient source including saliva, buccal cells, hair roots, blood, cord blood, amniotic fluid, interstitial fluid, peritoneal fluid, chorionic villus, and any other suitable cell or tissue sample with intact interphase nuclei or metaphase cells. The cells can be obtained from solid tissue as from a fresh or preserved organ or from a tissue sample or biopsy. The sample can contain compounds which are not naturally intermixed with the biological material such as preservatives, anticoagulants, buffers, fixatives, nutrients, antibiotics, or the like.

Methods for isolation of genomic DNA from these various sources are described in, for example, Kirby, *DNA Fingerprinting, An Introduction*, W.H. Freeman & Co. New York (1992). Genomic DNA can also be isolated from cultured primary or secondary cell cultures or from transformed cell lines derived from any of the aforementioned tissue samples.

Samples of animal RNA can also be used. RNA can be isolated from tissues expressing the Ghrelin gene as described in Sambrook et al., supra. RNA can be total cellular RNA, mRNA, poly A+RNA, or any combination thereof. For best results, the RNA is purified, but can also be unpurified cytoplasmic RNA. RNA can be reverse transcribed to form DNA which is then used as the amplification template, such that the PCR indirectly amplifies a specific population of RNA transcripts. See, e.g., Sambrook, supra, Kawasaki et al., Chapter 8 in *PCR Technology*, (1992) supra, and Berg et al., Hum. Genet. 85:655–658 (1990).

PCR Amplification

The most common means for amplification is polymerase chain reaction (PCR), as described in U.S. Pat. Nos. 4,683,195, 4,683,202, 4,965,188 each of which is hereby incorporated by reference. If PCR is used to amplify the target regions in blood cells, heparinized whole blood should be drawn in a sealed vacuum tube kept separated from other samples and handled with clean gloves. For best results, blood should be processed immediately after collection; if this is impossible, it should be kept in a sealed container at 4° C. until use. Cells in other physiological fluids may also be assayed. When using any of these fluids, the cells in the fluid should be separated from the fluid component by centrifugation.

Tissues should be roughly minced using a sterile, disposable scalpel and a sterile needle (or two scalpels) in a 5 mm Petri dish. Procedures for removing paraffin from tissue sections are described in a variety of specialized handbooks well known to those skilled in the art.

To amplify a target nucleic acid sequence in a sample by PCR, the sequence must be accessible to the components of the amplification system. One method of isolating target DNA is crude extraction which is useful for relatively large samples. Briefly, mononuclear cells from samples of blood, amniocytes from amniotic fluid, cultured chorionic villus cells, or the like are isolated by layering on sterile Ficoll-Hypaque gradient by standard procedures. Interphase cells are collected and washed three times in sterile phosphate buffered saline before DNA extraction. If testing DNA from peripheral blood lymphocytes, an osmotic shock (treatment of the pellet for 10 sec with distilled water) is suggested, followed by two additional washings if residual red blood cells are visible following the initial washes. This will prevent the inhibitory effect of the heme group carried by hemoglobin on the PCR reaction. If PCR testing is not performed immediately after sample collection, aliquots of $10^6$ cells can be pelleted in sterile Eppendorf tubes and the dry pellet frozen at $-20°$ C. until use.

The cells are resuspended ($10^6$ nucleated cells per 100 µl) in a buffer of 50 mM Tris-HCl (pH 8.3), 50 mM KCl 1.5 mM $MgCl_2$, 0.5% Tween 20, 0.5% NP40 supplemented with 100 µg/ml of proteinase K. After incubating at 56° C. for 2 hr. the cells are heated to 95° C. for 10 min to inactivate the proteinase K and immediately moved to wet ice (snap-cool). If gross aggregates are present, another cycle of digestion in the same buffer should be undertaken. Ten µl of this extract is used for amplification.

When extracting DNA from tissues, e.g., chorionic villus cells or confluent cultured cells, the amount of the above mentioned buffer with proteinase K may vary according to the size of the tissue sample. The extract is incubated for 4–10 hrs at 50°–60° C. and then at 95° C. for 10 minutes to inactivate the proteinase. During longer incubations, fresh proteinase K should be added after about 4 hr at the original concentration.

When the sample contains a small number of cells, extraction may be accomplished by methods as described in Higuchi, "Simple and Rapid Preparation of Samples for PCR", in *PCR Technology*, Ehrlich, H. A. (ed.), Stockton Press, New York, which is incorporated herein by reference. PCR can be employed to amplify target regions in very small numbers of cells (1000–5000) derived from individual colonies from bone marrow and peripheral blood cultures. The cells in the sample are suspended in 20 µl of PCR lysis buffer (10 mM Tris-HCl (pH 8.3), 50 mM KCl, 2.5 mM $MgCl_2$, 0.1 mg/ml gelatin, 0.45% NP40, 0.45% Tween 20) and frozen until use. When PCR is to be performed, 0.6 µl of proteinase K (2 mg/ml) is added to the cells in the PCR lysis buffer. The sample is then heated to about 60° C. and incubated for 1 hr. Digestion is stopped through inactivation of the proteinase K by heating the samples to 95° C. for 10 min and then cooling on ice.

A relatively easy procedure for extracting DNA for PCR is a salting out procedure adapted from the method described by Miller et al., *Nucleic Acids Res.* 16:1215 (1988), which is incorporated herein by reference. Mononuclear cells are separated on a Ficoll-Hypaque gradient. The cells are resuspended in 3 ml of lysis buffer (10 mM Tris-HCl, 400 mM NaCl, 2 mM $Na_2$ EDTA, pH 8.2). Fifty µl of a 20 mg/ml solution of proteinase K and 150 µl of a 20% SDS solution are added to the cells and then incubated at 37° C. overnight. Rocking the tubes during incubation will improve the digestion of the sample. If the proteinase K digestion is incomplete after overnight incubation (fragments are still visible), an additional 50 µl of the 20 mg/ml proteinase K solution is mixed in the solution and incubated for another night at 37° C. on a gently rocking or rotating platform. Following adequate digestion, one ml of a 6M NaCl solution is added to the sample and vigorously mixed. The resulting solution is centrifuged for 15 minutes at 3000 rpm. The pellet contains the precipitated cellular proteins, while the supernatant contains the DNA. The supernatant is removed to a 15 ml tube that contains 4 ml of isopropanol. The contents of the tube are mixed gently until the water and the alcohol phases have mixed and a white DNA precipitate has formed. The DNA precipitate is removed and dipped in a solution of 70% ethanol and gently mixed. The DNA precipitate is removed from the ethanol and air-dried. The precipitate is placed in distilled water and dissolved.

Kits for the extraction of high-molecular weight DNA for PCR include a Genomic isolation Kit A.S.A.P. (Boehringer Mannheim, Indianapolis, Ind.), Genomic DNA Isolation System (GIBCO BRL, Gaithersburg, Md.), Elu-Quik DNA Purification Kit (Schleicher & Schuell, Keene, N. H.), DNA Extraction Kit (Stratagene, LaJolla, Calif.), TurboGen Isolation Kit (Invitrogen, San Diego, Calif.), and the like. Use of these kits according to the manufacturer's instructions is generally acceptable for purification of DNA prior to practicing the methods of the present invention.

The concentration and purity of the extracted DNA can be determined by spectrophotometric analysis of the absorbance of a diluted aliquot at 260 nm and 280 nm. After extraction of the DNA, PCR amplification may proceed. The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In a particularly useful embodiment of PCR amplification, strand separation is achieved by heating the reaction to a sufficiently high temperature for a sufficient time to cause the denaturation of the duplex but not to cause an irreversible denaturation of the polymerase (see U.S. Pat. No. 4,965,188, incorporated herein by reference). Typical heat denaturation involves temperatures ranging from about 80° C. to 105° C. for times ranging from seconds to minutes. Strand separation, however, can be accomplished by any suitable denaturing method including physical, chemical, or enzymatic means. Strand separation may be induced by a helicase, for example, or an enzyme capable of exhibiting helicase activity. For example, the enzyme RecA has helicase activity in the presence of ATP. The reaction conditions suitable for strand separation by helicases are known in the art (see Kuhn Hoffman-Berling, 1978, CSH-Quantitative Biology, 43:63–67; and Radding, 1982, Ann. Rev. Genetics 16:405–436, each of which is incorporated herein by reference).

Template-dependent extension of primers in PCR is catalyzed by a polymerizing agent in the presence of adequate amounts of four deoxyribonucleotide triphosphates (typically dATP, dGTP, dCTP, and dTTP) in a reaction medium comprised of the appropriate salts, metal cations, and pH buffering systems. Suitable polymerizing agents are enzymes known to catalyze template-dependent DNA synthesis. In some cases, the target regions may encode at least a portion of a protein expressed by the cell. In this instance, mRNA may be used for amplification of the target region. Alternatively, PCR can be used to generate a cDNA library from RNA for further amplification, the initial template for primer extension is RNA. Polymerizing agents suitable for synthesizing a complementary, copy-DNA (cDNA) sequence from the RNA template are reverse transcriptase (RT), such as avian myeloblastosis virus RT, Moloney murine leukemia virus RT, or *Thermus thermophilus* (Tth) DNA polymerase, a thermostable DNA polymerase with reverse transcriptase activity marketed by Perkin Elmer Cetus, Inc. Typically, the RNA template is heat degraded during the first denaturation step after the initial reverse transcription step leaving only DNA template. Suitable polymerases for use with a DNA template include, for example, *E. coli* DNA polymerase I or its Klenow fragment, T4 DNA polymerase, Tth polymerase, and Taq polymerase, a heat-stable DNA polymerase isolated from *Thermus aquaticus* and commercially available from Perkin Elmer Cetus, Inc. The latter enzyme is widely used in the amplification and sequencing of nucleic acids. The reaction conditions for using Taq polymerase are known in the art and are described in Gelfand, 1989, PCR Technology, supra.

Allele Specific PCR

Allele-specific PCR differentiates between target regions differing in the presence of absence of a variation or polymorphism. PCR amplification primers are chosen which bind only to certain alleles of the target sequence. This method is described by Gibbs, Nucleic Acid Res. 17:12427–2448 (1989).

Allele Specific Oligonucleotide Screening Methods

Further diagnostic screening methods employ the allele-specific oligonucleotide (ASO) screening methods, as described by Saiki et al., Nature 324:163–166 (1986). Oligonucleotides with one or more base pair mismatches are generated for any particular allele. ASO screening methods detect mismatches between variant target genomic or PCR amplified DNA and non-mutant oligonucleotides, showing decreased binding of the oligonucleotide relative to a mutant oligonucleotide. Oligonucleotide probes can be designed that under low stringency will bind to both polymorphic forms of the allele, but which at high stringency, bind to the allele to which they correspond. Alternatively, stringency conditions can be devised in which an essentially binary response is obtained, i.e., an ASO corresponding to a variant form of the target gene will hybridize to that allele, and not to the wildtype allele.

Ligase Mediated Allele Detection Method

Target regions of a test subject's DNA can be compared with target regions in unaffected and affected family members by ligase-mediated allele detection. See Landegren et al., Science 241:107–1080 (1988). Ligase may also be used to detect point mutations in the ligation amplification reaction described in Wu et al., *Genomics* 4:560–569 (1989). The ligation amplification reaction (LAR) utilizes amplification of specific DNA sequence using sequential rounds of template dependent ligation as described in Wu, supra, and Barany, *Proc. Nat. Acad. Sci.* 88:189–193 (1990).

Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. DNA molecules melt in segments, termed melting domains, under conditions of increased temperature or denaturation. Each melting domain melts cooperatively at a distinct, base-specific melting temperature (TM). Melting domains are at least 20 base pairs in length, and may be up to several hundred base pairs in length.

Differentiation between alleles based on sequence specific melting domain differences can be assessed using polyacrylamide gel electrophoresis, as described in Chapter 7 of Erlich, ed., *PCR Technology, Principles and Applications for DNA Amplification*, W. H. Freeman and Co., New York (1992), the contents of which are hereby incorporated by reference.

Generally, a target region to be analyzed by denaturing gradient gel electrophoresis is amplified using PCR primers flanking the target region. The amplified PCR product is applied to a polyacrylamide gel with a linear denaturing gradient as described in Myers et al., *Meth. Enzymol.* 155:501–527 (1986), and Myers et al., in *Genomic Analysis, A Practical Approach*, K. Davies Ed. IRL Press Limited, Oxford, pp. 95–139 (1988), the contents of which are hereby incorporated by reference. The electrophoresis system is maintained at a temperature slightly below the Tm of the melting domains of the target sequences.

In an alternative method of denaturing gradient gel electrophoresis, the target sequences may be initially attached to a stretch of GC nucleotides, termed a GC clamp, as described in Chapter 7 of Erlich, supra. Preferably, at least 80% of the nucleotides in the GC clamp are either guanine or cytosine. Preferably, the GC clamp is at least 30 bases long. This method is particularly suited to target sequences with high Tm's.

Generally, the target region is amplified by the polymerase chain reaction as described above. One of the oligonucleotide PCR primers carries at its 5' end, the GC clamp region, at least 30 bases of the GC rich sequence, which is incorporated into the 5' end of the target region during amplification. The resulting amplified target region is run on an electrophoresis gel under denaturing gradient conditions as described above. DNA fragments differing by a single base change will migrate through the gel to different positions, which may be visualized by ethidium bromide staining.

Temperature Gradient Gel Electrophoresis

Temperature gradient gel electrophoresis (TGGE) is based on the same underlying principles as denaturing gradient gel electrophoresis, except the denaturing gradient is produced by differences in temperature instead of differences in the concentration of a chemical denaturant. Standard TGGE utilizes an electrophoresis apparatus with a temperature gradient running along the electrophoresis path. As samples migrate through a gel with a uniform concentration of a chemical denaturant, they encounter increasing temperatures. An alternative method of TGGE, temporal temperature gradient gel electrophoresis (TTGE or tTGGE) uses a steadily increasing temperature of the entire electrophoresis gel to achieve the same result. As the samples migrate through the gel the temperature of the entire gel increases, leading the samples to encounter increasing temperature as they migrate through the gel. Preparation of samples, including PCR amplification with incorporation of a GC clamp, and visualization of products are the same as for denaturing gradient gel electrophoresis.

Single-Strand Conformation Polymorphism Analysis

Target sequences or alleles at the Ghrelin locus can be differentiated using single-strand conformation polymorphism analysis, which identifies base differences by alteration in electrophoretic migration of single stranded PCR products, as described in Orita et al., *Proc. Nat. Acad. Sci.* 85:2766–2770 (1989). Amplified PCR products can be generated as described above, and heated or otherwise denatured, to form single stranded amplification products. Single-stranded nucleic acids may refold or form secondary structures which are partially dependent on the base sequence. Thus, electrophoretic mobility of single-stranded amplification products can detect base-sequence difference between alleles or target sequences.

Chemical or Enzymatic Cleavage of Mismatches

Differences between target sequences can also be detected by differential chemical cleavage of mismatched base pairs, as described in Grompe et al., *Am. J. Hum. Genet.* 48:212–222 (1991). In another method, differences between target sequences can be detected by enzymatic cleavage of mismatched base pairs, as described in Nelson et al., Nature Genetics 4:11–18 (1993). Briefly, genetic material from an animal and an affected family member may be used to generate mismatch free heterohybrid DNA duplexes. As used herein, "heterohybrid" means a DNA duplex strand comprising one strand of DNA from one animal, and a second DNA strand from another animal, usually an animal differing in the phenotype for the trait of interest. Positive selection for heterohybrids free of mismatches allows determination of small insertions, deletions or other polymorphisms that may be associated with Ghrelin polymorphisms.

Non-gel Systems

Other possible techniques include non-gel systems such as TAQMAN™ (Perkin Elmer). In this system oligonucleotide PCR primers are designed that flank the mutation in question and allow PCR amplification of the region. A third oligonucleotide probe is then designed to hybridize to the region containing the base subject to change between different alleles of the gene. This probe is labeled with fluorescent dyes at both the 5' and 3' ends. These dyes are chosen such that while in this proximity to each other the fluorescence of one of them is quenched by the other and cannot be detected. Extension by Taq DNA polymerase from the PCR primer positioned 5' on the template relative to the probe leads to the cleavage of the dye attached to the 5' end of the annealed probe through the 5' nuclease activity of the Taq DNA polymerase. This removes the quenching effect allowing detection of the fluorescence from the dye at the 3' end of the probe. The discrimination between different DNA sequences arises through the fact that if the hybridization of the probe to the template molecule is not complete, i.e., there is a mismatch of some form, the cleavage of the dye does not take place. Thus only if the nucleotide sequence of the oligonucleotide probe is completely complimentary to the template molecule to which it is bound will quenching be removed. A reaction mix can contain two different probe sequences each designed against different alleles that might be present thus allowing the detection of both alleles in one reaction.

Yet another technique includes an Invader Assay which includes isothermic amplification that relies on a catalytic release of fluorescence. See Third Wave Technology at http://worldwide web at twt.com.

Non-PCR Based DNA Diagnostics

The identification of a DNA sequence linked to Ghrelin can be made without an amplification step, based on polymorphisms including restriction fragment length polymorphisms in an animal and a family member. Hybridization probes are generally oligonucleotides which bind through complementary base pairing to all or part of a target nucleic acid. Probes typically bind target sequences lacking complete complementarity with the probe sequence depending on the stringency of the hybridization conditions. The probes are preferably labeled directly or indirectly, such that by assaying for the presence or absence of the probe, one can detect the presence or absence of the target sequence. Direct labeling methods include radioisotope labeling, such as with 32P or 35S. Indirect labeling methods include fluorescent tags, biotin complexes which may be bound to avidin or streptavidin, or peptide or protein tags. Visual detection methods include photoluminescents, Texas red, rhodamine and its derivatives, red leuco dye and 3,3',5,5'-tetramethylbenzidine (TMB), fluorescein, and its derivatives, dansyl, umbelliferone and the like or with horse radish peroxidase, alkaline phosphatase and the like.

Hybridization probes include any nucleotide sequence capable of hybridizing to the porcine chromosome where Ghrelin resides, and thus defining a genetic marker linked to Ghrelin, including a restriction fragment length polymorphism, a hypervariable region, repetitive element, or a variable number tandem repeat. Hybridization probes can be any gene or a suitable analog. Further suitable hybridization probes include exon fragments or portions of cDNAs or genes known to map to the relevant region of the chromosome.

Preferred tandem repeat hybridization probes for use according to the present invention are those that recognize a small number of fragments at a specific locus at high stringency hybridization conditions, or that recognize a larger number of fragments at that locus when the stringency conditions are lowered.

One or more additional restriction enzymes and/or probes and/or primers can be used. Additional enzymes, constructed probes, and primers can be determined by routine experimentation by those of ordinary skill in the art and are intended to be within the scope of the invention.

Although the methods described herein may be in terms of the use of a single restriction enzyme and a single set of primers, the methods are not so limited. One or more additional restriction enzymes and/or probes and/or primers can be used, if desired. Indeed in some situations it may be preferable to use combinations of markers giving specific haplotypes. Additional enzymes, constructed probes and primers can be determined through routine experimentation, combined with the teachings provided and incorporated herein.

According to the invention, polymorphisms in the Ghrelin gene have been identified which have an association with growth, appetite and fatness. The presence or absence of the markers, in one embodiment may be assayed by PCR RFLP analysis using the restriction endonucleases and amplification primers may be designed using analogous human, pig or other Ghrelin sequences due to the high homology in the region surrounding the polymorphisms, or may be designed using known Ghrelin gene sequence data as exemplified in GenBank or even designed from sequences obtained from linkage data from closely surrounding genes based upon the teachings and references herein. The sequences surrounding the polymorphism will facilitate the development of alternate PCR tests in which a primer of about 4–30 contiguous bases taken from the sequence immediately adjacent to the polymorphism is used in connection with a polymerase chain reaction to greatly amplify the region before treatment with the desired restriction enzyme. The primers need not be the exact complement; substantially equivalent sequences are acceptable. The design of primers for amplification by PCR is known to those of skill in the art and is discussed in detail in *Short Protocols in Molecular Biology*, $4^{th}$ ed., Ausubel Ed., John Wiley and Sons (1999). The following is a brief description of primer design.

Primer Design Strategy

Increased use of polymerase chain reaction (PCR) methods has stimulated the development of many programs to aid in the design or selection of oligonucleotides used as primers for PCR. Four examples of such programs that are freely available via the Internet are: PRIMER by Mark Daly and Steve Lincoln of the Whitehead Institute (UNIX, VMS, DOS, and Macintosh), Oligonucleotide Selection Program (OSP) by Phil Green and LaDeana Hiller of Washington University in St. Louis (UNIX, VMS, DOS, and Macintosh), PGEN by Yoshi (DOS only), and Amplify by Bill Engels of the University of Wisconsin (Macintosh only). Generally these programs help in the design of PCR primers by searching for bits of known repeated-sequence elements and then optimizing the $T_m$ by analyzing the length and GC content of a putative primer. Commercial software is also available and primer selection procedures are rapidly being included in most general sequence analysis packages.

Sequencing and PCR Primers

Designing oligonucleotides for use as either sequencing or PCR primers requires selection of an appropriate sequence that specifically recognizes the target, and then testing the sequence to eliminate the possibility that the oligonucleotide will have a stable secondary structure. Inverted repeats in the sequence can be identified using a repeat-identification or RNA-folding program such as those described above (see prediction of Nucleic Acid Structure). If a possible stem structure is observed, the sequence of the primer can be shifted a few nucleotides in either direction to minimize the predicted secondary structure. The sequence of the oligonucleotide should also be compared with the sequences of both strands of the appropriate vector and insert DNA. Obviously, a sequencing primer should only have a single match to the target DNA. It is also advisable to exclude primers that have only a single mismatch with an undesired target DNA sequence. For PCR primers used to amplify genomic DNA, the primer sequence should be compared to the sequences in the GenBank database to determine if any significant matches occur. If the oligonucleotide sequence is present in any known DNA sequence or, more importantly, in any known repetitive elements, the primer sequence should be changed.

The methods and materials of the invention may also be used more generally to evaluate pig DNA, genetically type individual pigs, and detect genetic differences in pigs. In particular, a sample of pig genomic DNA may be evaluated by reference to one or more controls to determine if a polymorphism in the Ghrelin gene is present. Preferably, RFLP analysis is performed with respect to the pig Ghrelin gene, and the results are compared with a control. The control is the result of a RFLP analysis of the pig Ghrelin gene of a different pig where the polymorphism of the pig Ghrelin gene is known. Similarly, the Ghrelin genotype of a pig may be determined by obtaining a sample of its genomic DNA, conducting RFLP analysis of the Ghrelin gene in the DNA, and comparing the results with a control. Again, the control is the result of RFLP analysis of the Ghrelin gene of a different pig. The results genetically type the pig by specifying the polymorphism(s) in its Ghrelin gene. Finally, genetic differences among pigs can be detected by obtaining samples of the genomic DNA from at least two pigs, identifying the presence or absence of a polymorphism in the Ghrelin gene, and comparing the results.

These assays are useful for identifying the genetic markers relating to growth, appetite and fatness, as discussed above, for identifying other polymorphisms in the Ghrelin gene that may be correlated with other characteristics, such as litter size and for the general scientific analysis of pig genotypes and phenotypes.

The examples and methods herein disclose certain genes which have been identified to have a polymorphism which is associated either positively or negatively with a beneficial trait that will have an effect on growth, appetite and fatness for animals carrying this polymorphism. The identification of the existence of a polymorphism within a gene is often made by a single base alternative that results in a restriction site in certain allelic forms. A certain allele, however, as demonstrated and discussed herein, may have a number of base changes associated with it that could be assayed for which are indicative of the same polymorphism (allele). Further, other genetic markers or genes may be linked to the polymorphisms disclosed herein so that assays may involve identification of other genes or gene fragments, but which ultimately rely upon genetic characterization of animals for the same polymorphism. Any assay which sorts and identifies animals based upon the allelic differences disclosed herein are intended to be included within the scope of this invention.

Linkage Analysis

Linkage analysis may be performed alone, or in combination with direct detection of phenotypically evident polymorphisms. The use of microsatellite markers for genotyping is well documented. For examples, see Mansfield et al. (1994) Genomics 24:225–233; and Ziegle et al. (1992) Genomics 14:1026–1031. The use of SNPs for genotyping is illustrated in Underhill et al. (1996) Proc. Natl. Acad. Sci. USA 93:196–200.

Genetic linkage maps show the relative locations of specific DNA markers along a chromosome. Any inherited physical or molecular characteristic that differs among individuals and is easily detectable in the laboratory is a potential genetic marker. DNA sequence polymorphisms are useful markers because they are plentiful and easy to characterize precisely. Many such polymorphisms are located in non-coding regions and do not affect the phenotype of the organism, yet they are detectable at the DNA level and can be used as markers. Examples include restriction fragment length polymorphisms (RFLPs), which reflect sequence variations in DNA sites or differences in the length of the product, which can be cleaved by DNA restriction enzymes, microsatellite markers, which are short repeated sequences that vary in the number of repeated units, single nucleotide polymorphisms (SNPs), and the like.

The "linkage" aspect of the map is a measure of how frequently two markers are inherited together. The closer the markers are to each other physically, the less likely a recombination event will fall between and separate them. Recombination frequency thus provides an estimate of the distance between two markers. The value of the genetic map is that an inherited trait can be located on the map by following the inheritance of a DNA marker present in affected animals, but absent in unaffected animals, even though the molecular basis for the trait may not yet be understood.

An emerging class of marker for genetic analysis of the single nucleotide polymorphism, and other simple polymorphisms, e.g. deletions, double nucleotide polymorphisms. SNPs are generally biallelic systems, that is, there are two alleles that a population may have for any particular marker. This means that the information content per SNP marker is relatively low when compared to microsatellite markers, which may have upwards of 10 alleles. SNPs also tend to be very population-specific; a marker that is polymorphic in one population may not be very polymorphic in another.

SNP markers offer a number of benefits that will make them an increasingly valuable tool. SNPs, found approximately every kilobase (see Wang et al. (1998) Science 280:1077–1082), offer the potential for generating very high density genetic maps, which will be extremely useful for developing haplotyping systems for genes or regions of interest, and because of the nature of SNPs, they may in fact be the polymorphisms associated with the traits under study. The low mutation rate of SNPs also makes them excellent markers for studying complex genetic traits.

One of skill in the art, once a polymorphism has been identified and a correlation to a particular trait established, will understand that there are many ways to genotype animals for this polymorphism. The design of such alternative tests merely represent optimization of parameters known to those of skill in the art and are intended to be within the scope of this invention as fully described herein.

The following examples serve to better illustrate the invention described herein and are not intended to limit the invention in any way. Those skilled in the art will recognize that there are several different parameters which may be altered using routine experimentation and are intended to be within the scope of this invention.

EXAMPLE 1

Ghrelin: PCR-RFLP Tests

```
Primers for Mix 1: 450 bp
                                        (SEQ ID NO:13)
GHR-1F:    5' CAG GAA GAC CAG CTG AGG C 3'

(SEQ ID NO:14)
GHR-2R:    5' GAA CCG GAT TTC CAG CTT GT 3'

Primers for Mix 2: 1100 bp
                                        (SEQ ID NO:15)
GHR-3F:    GTT GGG ATC AAG TTG TCA GG 3'

(SEQ ID NO:16)
GHR-4R:    CCT CAG AGC TGG GTG TGA TA 3'
```

PCR conditions:

| Mix 1: | | Mix 2: | |
|---|---|---|---|
| 10X Promega Buffer | 1.0 µL | 10X Promega Buffer | 1.0 µL |
| 25 mM MgCl$_2$ | 0.6 µL | 25 mM MgCl$_2$ | 0.5 µL |
| dNTPs mix (2.5 mM each) | 0.5 µL | dNTPs mix (2.5 mM each) | 0.5 µL |
| 25 pmol/µL GHR-1F | 0.1 µL | 25 pmol/µL GHR-3F | 0.1 µL |
| 25 pmol/µL GHR-2R | 0.1 µL | 25 pmol/µL GHR-4R | 0.1 µL |
| dd sterile H$_2$O | 7.4 µL | dd sterile H$_2$O | 7.5 µL |
| Taq Polymerase (5 U/µL) | 0.07 µL | Taq Polymerase (5 U/µL) | 0.07 µL |
| Genomic DNA (12.5 ng/µL) | 1.0 µL | Genomic DNA (12.5 ng/µL) | 1.0 µL |

1. Ran the following program: 94° C. for 2 min; 35 cycles of 94° C. for 30 sec, 54° C. (Mix 1) and 58° C. (Mix 2) 1 min, and 72° C. 1 min 30 sec; followed by a final extension at 72° C. for 10 min.

2. Checked 3 µL of the PCR reaction on a standard 1% agarose gel to confirm amplification success and clean negative control.

Digestion Reactions:

Added 5 µL to each reaction tube containing the DNA. Incubated at the recommended temperature from the manufacture for at least 4 hours to overnight. Mixed loading dyes with digestion reaction and loaded the total volume on a 3% agarose gel.

1. MspI Polymorphism of Mix 1 PCR Product

| | |
|---|---|
| PCR product | 5.0 µL |
| 10X NE Buffer 2 | 1.0 µL |
| BSA (10 mg/ml) | 0.3 µL |
| MspI enzyme (20 U/µL) | 0.3 µL |
| dd sterile H$_2$O | 3.6 µL |

Figure 2A:
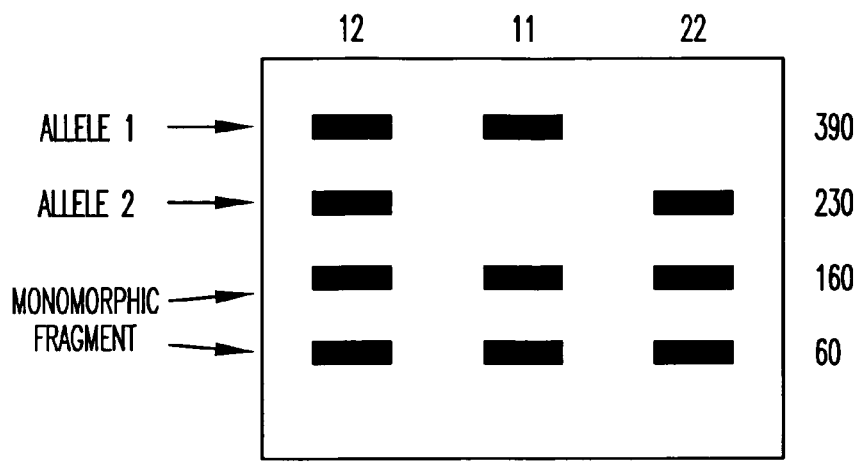
FIGS. 2A–H are the results of the PCR-RFLP test demonstrating the ability to detect the alleles.

Results from the MspI digestion of Mix 1 are shown in FIG. 2A.

2. AluI polymorphism of the Mix 1 PCR Product

This test was not able to determine between 12 and 22 genotypes because the binding site of the GHR-2R primer contains the polymorphism.

| | |
|---|---|
| PCR product | 5.0 µL |
| 10X NE Buffer 2 | 1.0 µL |
| BSA (10 mg/ml) | 0.3 µL |
| AluI enzyme (10 U/µL) | 0.5 µL |
| dd sterile H$_2$O | 3.5 µL |

Figure 2B:
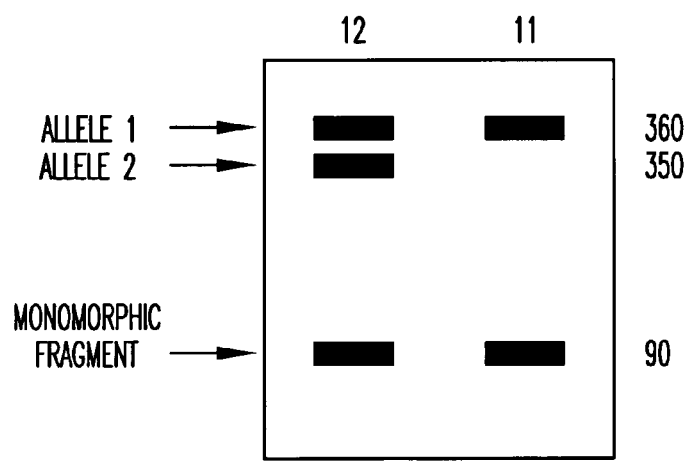

Results from the AluI digestion of Mix 1 are shown in FIG. 2B.

3. RsaI Polymorphism of the Mix 2 PCR Product

| | |
|---|---|
| PCR product | 5.0 µL |
| 10X NE Buffer 1 | 1.0 µL |
| BSA (10 mg/ml) | 0.3 µL |
| RsaI enzyme (10 U/µL) | 0.5 µL |
| dd sterile H$_2$O | 3.5 µL |

Figure 2C:
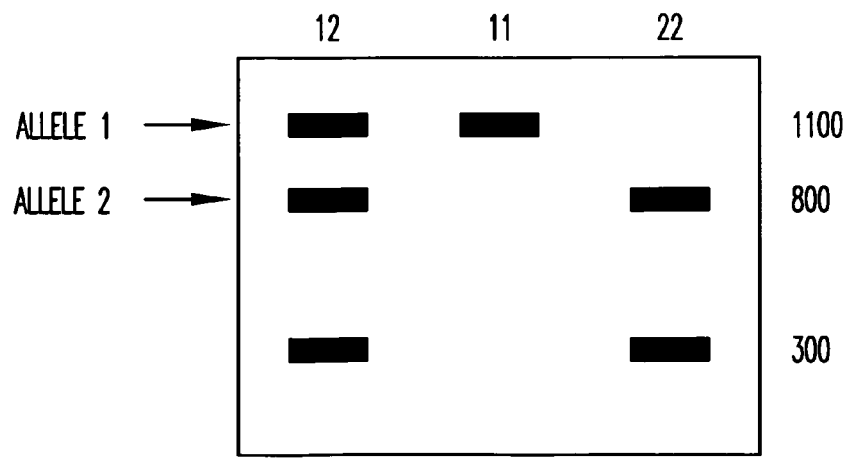

Results from the RsaI digestion of the Mix 2 are shown in FIG. 2C.

4. BsrI Polymorphism of the Mix 2 PCR Product

| | |
|---|---|
| PCR product | 5.0 μL |
| 10X NE Buffer 3 | 1.0 μL |
| BSA (10 mg/ml) | 0.3 μL |
| BsrI enzyme (10 U/μL) | 0.5 μL |
| dd sterile H₂O | 3.5 μL |

Figure 2D:
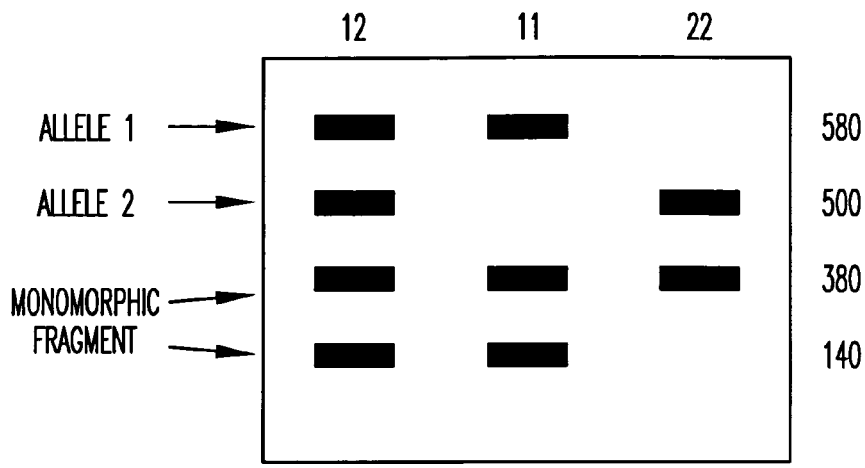
Figure 2E:
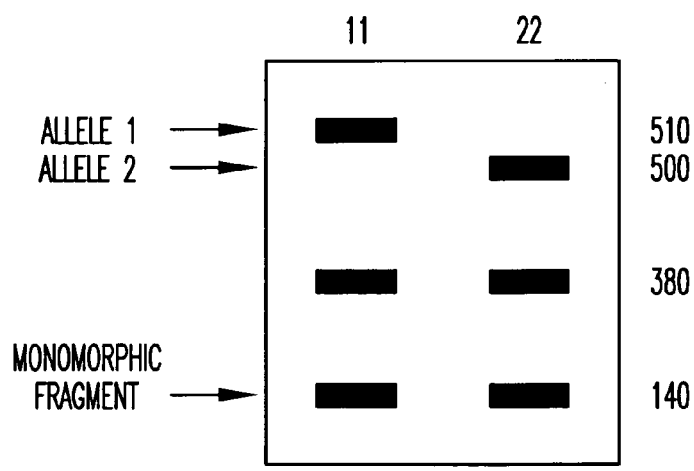

Results from the Type I of the BsrI digestion of Mix 2 are shown in FIG. 2D.
Results from the Type II of the BsrI digestion of Mix 2 are shown in FIG. 2E.

5. BglII Polymorphism of the Mix 2 PCR Product

| | |
|---|---|
| PCR product | 5.0 μL |
| 10X NE Buffer 3 | 1.0 μL |
| BSA (10 mg/ml) | 0.3 μL |
| BglII enzyme (20 U/μL) | 0.3 μL |
| dd sterile H₂O | 3.6 μL |

Figure 2F:
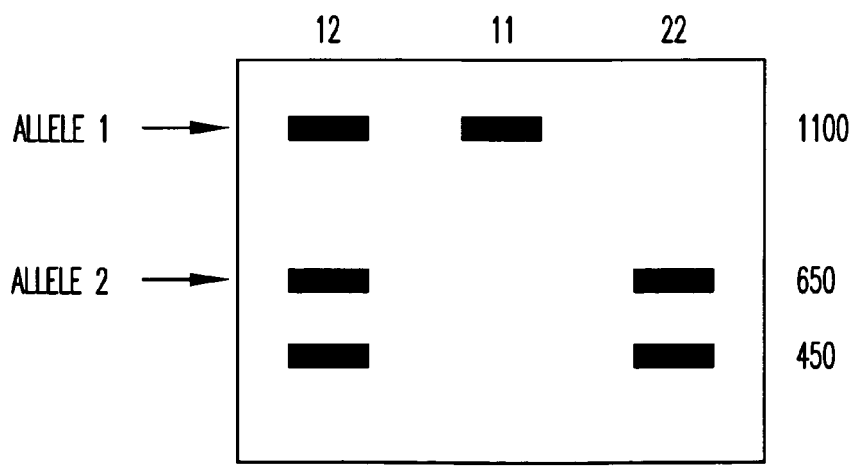

Results from the BglII digestion of Mix 2 are shown in FIG. 2F.

6. AluI Polymorphism of the Mix 2 PCR Product

| | |
|---|---|
| PCR product | 5.0 μL |
| 10X NE Buffer 2 | 1.0 μL |
| BSA (10 mg/ml) | 0.3 μL |
| AluI enzyme (10 U/μL) | 0.5 μL |
| dd sterile H₂O | 3.5 μL |

Figure 2G:
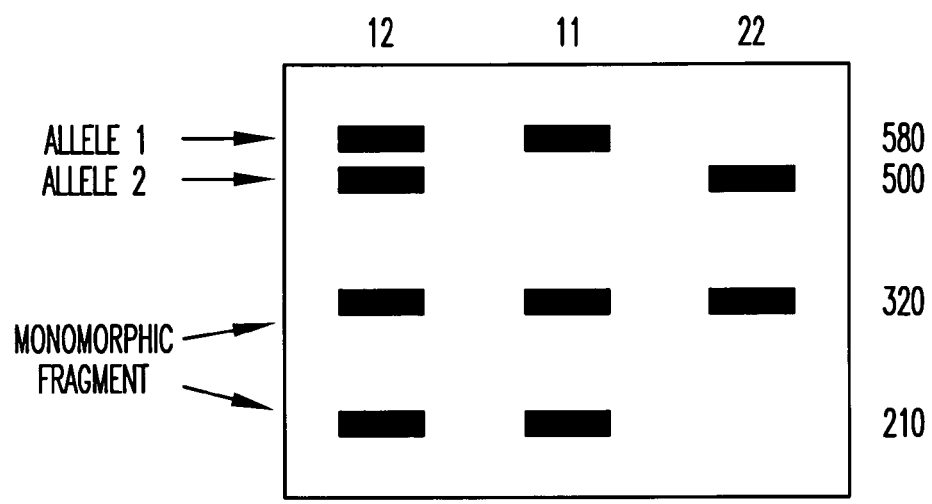

Results from the AluI digestion of Mix 2 are shown in FIG. 2G.

7. ApaI Polymorphism of the Mix 1 PCR Product: Incubated at 25° C.

| | |
|---|---|
| PCR product | 5.0 μL |
| 10X NE Buffer 4 | 1.0 μL |
| BSA (10 mg/ml) | 0.3 μL |
| ApaI enzyme (10 U/μL) | 0.5 μL |
| dd sterile H₂O | 3.5 μL |

Figure 2H:
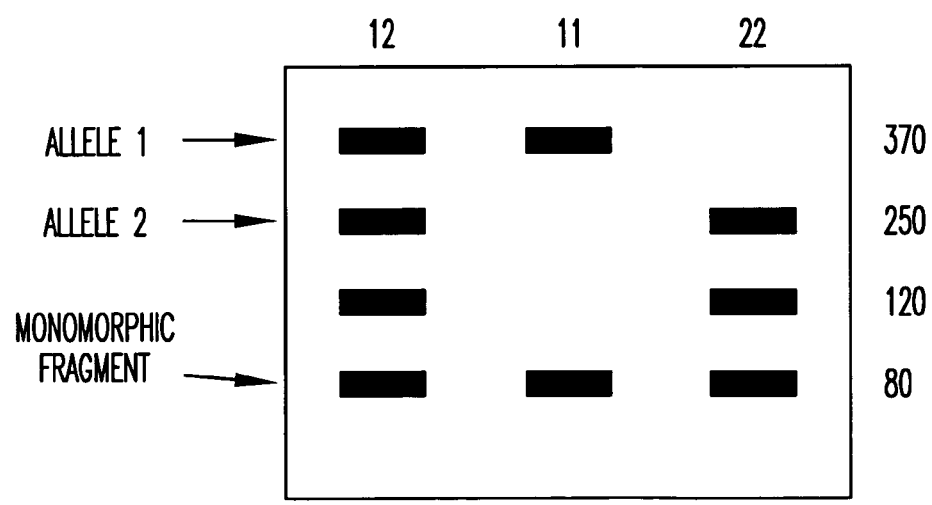

Results from the ApaI digestion of Mix 1 are shown in FIG. 2H.

EXAMPLE 2

Multi-point Analysis

It was found that the porcine ghrelin locus is located within important QTL regions for fatness and meat quality traits disclosed herein. The Type I of the BsrI polymorphism was tested.

Berkshire and Yorkshire Crossed Reference Family:
1. Multi-point Analysis (Without Ghrelin)

Sex_average map (recomb. Frac., Kosambi cM):

| | | | | | |
|---|---|---|---|---|---|
| 0 | sw1941 | | | | 0.0 |
| | | 0.12 | | 12.8 | |
| 8 | swr428 | | | | 12.8 |
| | | 0.10 | | 10.1 | |
| 1 | sw1407 | | | | 22.9 |
| | | 0.11 | | 11.6 | |
| 2 | sw344 | | | | 34.5 |
| | | 0.13 | | 13.5 | |
| 3 | s0068 | | | | 48.1 |
| | | 0.12 | | 12.2 | |
| 4 | sw398 | | | | 60.3 |
| | | 0.15 | | 15.2 | |
| 5 | sw1056 | | | | 75.5 |
| | | 0.06 | | 5.9 | |
| 7 | sw2440 | | | | 81.4 |
| | | 0.18 | | 18.5 | |
| 6 | sw2097 | | | | 99.9 |

*denotes recomb. frac. held fixed in this analysis
$\log_{10}$ like = −1134.549

2. Two-Point Linkage Analysis of Ghrelin

| Locus 1 | Locus 2 | Rec Fr. | LOD Score |
|---|---|---|---|
| s0068 | ghr | 0.08 | 50.88 |
| sw1407 | ghr | 0.21 | 20.13 |
| sw2440 | ghr | 0.28 | 10.41 |
| sw344 | ghr | 0.11 | 37.97 |
| sw398 | ghr | 0.16 | 26.76 |
| swr428 | ghr | 0.26 | 13.55 |

3. Multi-point Analysis of Ghrelin

Sex_averaged map (recomb. frac., Kosambi cM):

| | | | | | |
|---|---|---|---|---|---|
| 0 | sw1941 | | | | 0.0 |
| | | 0.12 | | 12.8 | |
| 8 | swr428 | | | | 12.8 |
| | | 0.10 | | 10.1 | |
| 1 | sw1407 | | | | 22.9 |
| | | 0.11 | | 11.7 | |
| 2 | sw344 | | | | 34.6 |
| | | 0.10 | | 9.7 | |
| 9 | ghr | | | | 44.2 |
| | | 0.07 | | 6.7 | |
| 3 | s0068 | | | | 50.9 |
| | | 0.12 | | 12.2 | |
| 4 | sw398 | | | | 63.1 |
| | | 0.15 | | 15.2 | |
| 5 | sw1056 | | | | 78.3 |
| | | 0.06 | | 5.9 | |
| 7 | sw2440 | | | | 84.2 |
| | | 0.18 | | 18.5 | |
| 6 | sw2097 | | | | 102.8 |

*denotes recomb. frac. held fixed in this analysis

EXAMPLE 3

Multi-point Analysis Tests were Done on the MspI Polymorphism

PiGMaP Reference Family:

| Locus 1 | Locus 2 | Rec Fr. | LOD Score |
|---|---|---|---|
| Ghr | Ghr | 0.00 | 13.25 |
| PPARG | Ghr | 0.00 | 4.82 |
| RAF1 | Ghr | 0.00 | 3.61 |
| S0021 | Ghr | 0.00 | 9.33 |
| S0068 | Ghr | 0.10 | 6.06 |
| S0084 | Ghr | 0.06 | 8.00 |
| S0222 | Ghr | 0.05 | 7.65 |
| S0223 | Ghr | 0.00 | 12.94 |

-continued

| Locus 1 | Locus 2 | Rec Fr. | LOD Score |
|---------|---------|---------|-----------|
| S0281   | Ghr     | 0.00    | 12.04     |
| S0293   | Ghr     | 0.12    | 4.89      |
| S0393   | Ghr     | 0.00    | 4.21      |
| SJ0044  | Ghr     | 0.16    | 4.94      |
| SJ015   | Ghr     | 0.00    | 5.12      |
| SSCP142 | Ghr     | 0.08    | 3.90      |
| SW864   | Ghr     | 0.15    | 3.89      |
| SW937   | Ghr     | 0.00    | 13.25     |
| TF-2    | Ghr     | 0.00    | 3.01      |

Sex_averaged map (recomb. frac., Kosambi cM):

| 14 | S0021  |       |      | 0.0  |
|----|--------|-------|------|------|
|    |        | 0.02  | 2.5  |      |
| 27 | S0223  |       |      | 2.5  |
|    |        | 0.00  | 0.0  |      |
| 61 | Ghr    |       |      | 2.5  |
|    |        | 0.00  | 0.0  |      |
| 11 | PPARG  |       |      | 2.5  |
|    |        | 0.02  | 1.5  |      |
| 60 | TF-2   |       |      | 4.0  |
|    |        | 0.00  | 0.0  |      |
| 57 | SW937  |       |      | 4.0  |
|    |        | 0.04  | 4.4  |      |
| 15 | S0068  |       |      | 8.4  |
|    |        | 0.00* | 0.0  |      |
| 16 | S0068  |       |      | 8.4  |
|    |        | 0.36  | 45.3 |      |
| 34 | S0289  |       |      | 53.7 |

*denotes recomb. frac. held fixed in this analysis
$\log_{10}$_like = −76.560

Sex averaged map (recomb. frac., Kosambi cM):

| 14 | S0021  |       |      | 0.0  |
|----|--------|-------|------|------|
|    |        | 0.02  | 2.5  |      |
| 27 | S0223  |       |      | 2.5  |
|    |        | 0.00  | 0.0  |      |
| 11 | PPARG  |       |      | 2.5  |
|    |        | 0.01  | 0.9  |      |
| 61 | Ghr    |       |      | 3.4  |
|    |        | 0.01  | 0.7  |      |
| 60 | TF-2   |       |      | 4.0  |
|    |        | 0.00  | 0.0  |      |
| 57 | SW937  |       |      | 4.0  |
|    |        | 0.04  | 4.4  |      |
| 15 | S0068  |       |      | 8.4  |
|    |        | 0.00* | 0.0  |      |
| 16 | S0068  |       |      | 8.4  |
|    |        | 0.36  | 45.3 |      |
| 34 | S0289  |       |      | 53.7 |

*denotes recomb. frac. held fixed in this analysis
$\log_{10}$_like = −76.558

Sex averaged map (recomb. frac., Kosambi cM):

| 14 | S0021  |       |      | 0.0  |
|----|--------|-------|------|------|
|    |        | 0.02  | 2.5  |      |
| 27 | S0223  |       |      | 2.5  |
|    |        | 0.00  | 0.0  |      |
| 11 | PPARG  |       |      | 2.5  |
|    |        | 0.02  | 1.6  |      |
| 60 | TF-2   |       |      | 4.0  |
|    |        | 0.00  | 0.0  |      |
| 61 | Ghr    |       |      | 4.0  |
|    |        | 0.00  | 0.0  |      |
| 57 | SW937  |       |      | 4.0  |
|    |        | 0.04  | 4.4  |      |
| 15 | S0068  |       |      | 8.4  |
|    |        | 0.00* | 0.0  |      |
| 16 | S0068  |       |      | 8.4  |
|    |        | 0.36  | 45.3 |      |
| 34 | S0289  |       |      | 53.7 |

*denotes recomb. frac. held fixed in this analysis
$\log_{10}$_like = −76.553

EXAMPLE 4

Association Analysis Between Genotypes of Ghrelin and Some Meat Quality Traits Association between Ghrelin genotype and carcass traits in a line selected for meat quality. Effects were found for genotype on yield of loin and ham (L/H_bone in weight) and marbling and fatness. All results were from mixed model with sire as random effect and slaughterdate as fixed.

LSmeans Significance Levels:

| a–b | $p < .3$    |
| c–d | $p < .1$    |
| e–f | $p < .05$   |
| g–h | $p < .01$   |
| i–j | $p < .005$  |
| k–l | $p < .001$  |
| m–n | $p < .0005$ |
| o–p | $p < .0001$ |

Geno p:p Value for Genotype in the Model TRAIT=Sire+Slaughterdate+Genotype

TABLE 1

Association results between the genotypes of Ghrelin BsrI and carcass traits

| Trait | No. of animals | | | LS means (s.e.) | | | Geno p |
|-------|----|----|----|----|----|----|----|
|       | 11 | 12 | 22 | 11 | 12 | 22 |    |
| L_BINWT | 9 | 13 | 28 | 16.84 (0.60) e | 18.81 (0.52) f | 17.44 (0.35) e | 0.06 |
| marbling | 10 | 16 | 35 | 3.65 (0.29) c e | 2.91 (0.25) d | 2.88 (0.17) f | 0.07 |

TABLE 1-continued

Association results between the genotypes of Ghrelin BsrI and carcass traits

| Trait | No. of animals | | | LS means (s.e.) | | | Geno p |
|---|---|---|---|---|---|---|---|
| | 11 | 12 | 22 | 11 | 12 | 22 | |
| H_BINWT | 9 | 13 | 27 | 22.11 90.39 a e | 21.23 (0.30) b | 21.18 (0.21) f | 0.10 |
| Probe fat | 10 | 24 | 40 | 23.66 (1.37) e a | 27.43 (1.00) f a | 25.74 (0.76) b | 0.08 |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims. Thus, many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims.

REFERENCES

Tschop, M., Smiley D. L., Helman, M. L., Ghrelin induces adiposity in rodents, *Nature* (2000) 407: 908–913.

Nakazato, M., Murakami, N., Yukari, D., Kojima, M., Matsuo, H., Kangawa, K., Matsukura, S., A role for ghrelin in the central regulation of feeding, *Nature* (2001), 409: 194–198.

What is claimed is:

1. A method for indirect selection of a polymorphism in a Ghrelin gene associated with the traits of growth, appetite, and fatness comprising:
    selecting specific alleles of an alternative DNA marker associated with said Ghrelin gene sequence as set forth in SEQ ID NO: 11 or 12, wherein said gene is associated with the traits of growth, appetite, and fatness;
    making an indirect selection of a polymorphism; and
    establishing linkage between the specific allele of the alternative DNA and alleles of the DNA marker associated with the traits of growth, appetite, and fatness.

2. A method of identifying a polymorphism associated with growth, appetite, and fatness in a pig comprising:
    breeding male and female pigs of the same breed or breed cross or similar genetic linkages to obtain offspring;
    determining growth, appetite, and fatness of said offspring;
    determining the polymorphism in the Ghrelin gene as set forth in SEQ ID NOS: 11 or 12 of said offspring;
    and associating said growth, appetite, and fatness of said offspring with said polymorphism, thereby identifying a polymorphism for growth, appetite, and fatness.

3. The method of claim 2 further comprising selecting pigs for breeding which are predicted to have increased growth, appetite, and fatness by said polymorphism.

4. The method of claim 2 wherein the step of determining the polymorphism in the Ghrelin gene comprises analyzing a genetic sample obtained from said offspring for a polymorphism identified by a restriction enzyme site selected from the group consisting of MspI, ApaI AluI, RsaI, BsrI, and BglII.

5. A method of identifying a polymorphism correlated with growth, appetite, and fatness comprising the steps of:
obtaining a sample of genetic material from a pig, said sample comprising a Ghrelin gene as set forth in SEQ ID NO: 11 or 12;
assaying for said Ghrelin gene presented in said sample for a polymorphism;
correlating whether a statistically significant association exists between said polymorphism and growth, appetite, and fatness in a pig of a particular breed, population or group whereby said pig can be characterized for said polymorphism.

6. The method of claim 5 wherein said polymorphism is identified by a restriction enzyme site selected from the group consisting of MspI, ApaI AluI, RsaI, BsrI, and BglII.

* * * * *

```
SEQUENCE LISTING

<160> NUMBER OF SEQ ID NOS: 16

<210> SEQ ID NO 1
<211> LENGTH: 60
<212> TYPE: PRT
<213> ORGANISM: Mouse

<400> SEQUENCE: 1

Met Leu Ser Ser Gly Thr Ile Cys Ser Leu Leu Leu Leu Ser Met Leu
1               5                   10                  15

Trp Met Asp Met Ala Met Ala Gly Ser Ser Phe Leu Ser Pro Glu His
            20                  25                  30

Gln Lys Ala Gln Gln Arg Lys Glu Ser Lys Lys Pro Pro Ala Lys Leu
        35                  40                  45

Gln Pro Arg Ala Leu Glu Gly Trp Leu His Pro Glu
    50                  55                  60

<210> SEQ ID NO 2
<211> LENGTH: 59
<212> TYPE: PRT
<213> ORGANISM: Bovine

<400> SEQUENCE: 2

Met Pro Ala Pro Trp Thr Ile Cys Ser Leu Leu Leu Leu Ser Val Leu
1               5                   10                  15

Cys Met Asp Leu Ala Met Ala Gly Ser Ser Phe Leu Ser Pro Glu His
            20                  25                  30

Gln Lys Leu Gln Arg Lys Glu Ala Lys Lys Pro Ser Gly Arg Leu Lys
        35                  40                  45

Pro Arg Thr Leu Glu Gly Gln Phe Asp Pro Glu
    50                  55
```

<210> SEQ ID NO 3
<211> LENGTH: 60
<212> TYPE: PRT
<213> ORGANISM: Human

<400> SEQUENCE: 3

Met Pro Ser Pro Gly Thr Val Cys Ser Leu Leu Leu Gly Met Leu
1               5                   10                  15

Trp Leu Asp Leu Ala Met Ala Gly Ser Ser Phe Leu Ser Pro Glu His
            20                  25                  30

Gln Arg Val Gln Gln Arg Lys Glu Ser Lys Lys Pro Ala Lys Leu
        35                  40                  45

Gln Pro Arg Ala Leu Ala Gly Trp Leu Arg Pro Glu
    50                  55                  60

<210> SEQ ID NO 4
<211> LENGTH: 61
<212> TYPE: PRT
<213> ORGANISM: Porcine

<400> SEQUENCE: 4

Met Pro Ser Thr Gly Thr Ile Cys Ser Leu Leu Leu Ser Val Leu
1               5                   10                  15

Leu Met Ala Asp Leu Ala Met Ala Gly Ser Ser Phe Leu Ser Pro Glu
            20                  25                  30

His Gln Lys Val Gln Gln Arg Lys Glu Ser Lys Lys Pro Ala Ala Lys
        35                  40                  45

Leu Lys Pro Arg Ala Leu Glu Gly Trp Leu Gly Pro Glu
    50                  55                  60

<210> SEQ ID NO 5
<211> LENGTH: 61
<212> TYPE: PRT
<213> ORGANISM: Porcine

<400> SEQUENCE: 5

Met Pro Ser Thr Gly Thr Ile Cys Ser Leu Leu Leu Ser Val Leu
1               5                   10                  15

Leu Met Ala Asp Leu Ala Met Ala Gly Ser Ser Phe Leu Ser Pro Glu
            20                  25                  30

His Gln Lys Val Gln Gln Arg Lys Glu Ser Lys Lys Pro Ala Ala Lys
        35                  40                  45

Leu Lys Pro Arg Ala Leu Glu Gly Trp Leu Gly Pro Glu
    50                  55                  60

<210> SEQ ID NO 6
<211> LENGTH: 57
<212> TYPE: PRT
<213> ORGANISM: Mouse

<400> SEQUENCE: 6

Asp Arg Gly Gln Ala Glu Glu Thr Glu Glu Leu Glu Ile Arg Phe
1               5                   10                  15

Asn Ala Pro Phe Asp Val Gly Ile Lys Leu Ser Gly Ala Gln Tyr Gln
            20                  25                  30

Gln His Gly Arg Ala Leu Gly Lys Phe Leu Gln Asp Ile Leu Trp Glu
        35                  40                  45

Glu Val Lys Glu Ala Pro Ala Asp Lys

```
            50                  55

<210> SEQ ID NO 7
<211> LENGTH: 57
<212> TYPE: PRT
<213> ORGANISM: Bovine

<400> SEQUENCE: 7

Val Gly Ser Gln Ala Glu Gly Ala Glu Asp Glu Leu Glu Ile Arg Phe
1               5                   10                  15

Asn Ala Pro Phe Asn Ile Gly Ile Lys Leu Ala Gly Ala Gln Ser Leu
            20                  25                  30

Gln His Gly Gln Thr Leu Gly Lys Phe Leu Gln Asp Ile Leu Trp Glu
        35                  40                  45

Glu Ala Glu Glu Thr Leu Ala Asn Glu
    50                  55

<210> SEQ ID NO 8
<211> LENGTH: 57
<212> TYPE: PRT
<213> ORGANISM: Human

<400> SEQUENCE: 8

Asp Gly Gly Gln Ala Glu Gly Ala Glu Asp Glu Leu Glu Val Arg Phe
1               5                   10                  15

Asn Ala Pro Phe Asp Val Gly Ile Lys Leu Ser Gly Val Gln Tyr Gln
            20                  25                  30

Gln His Ser Gln Ala Leu Gly Lys Phe Leu Gln Asp Ile Leu Trp Glu
        35                  40                  45

Glu Ala Lys Glu Ala Pro Ala Asp Lys
    50                  55

<210> SEQ ID NO 9
<211> LENGTH: 57
<212> TYPE: PRT
<213> ORGANISM: Porcine

<400> SEQUENCE: 9

Asp Ser Gly Glu Val Glu Gly Thr Glu Asp Lys Leu Glu Ile Arg Phe
1               5                   10                  15

Asn Ala Pro Cys Asp Val Gly Ile Lys Leu Ser Gly Ala Gln Ser Asp
            20                  25                  30

Gln His Gly Gln Pro Leu Gly Lys Phe Leu Gln Asp Ile Leu Trp Glu
        35                  40                  45

Glu Val Thr Glu Ala Pro Ala Asp Lys
    50                  55

<210> SEQ ID NO 10
<211> LENGTH: 57
<212> TYPE: PRT
<213> ORGANISM: Porcine
<220> FEATURE:
<221> NAME/KEY: MISC_FEATURE
<223> OTHER INFORMATION: N is an amino acid change

<400> SEQUENCE: 10

Asp Ser Gly Glu Val Glu Gly Thr Glu Asp Asn Leu Glu Ile Arg Phe
1               5                   10                  15

Asn Ala Pro Cys Asp Val Gly Ile Lys Leu Ser Gly Ala Gln Ser Asp
            20                  25                  30
```

```
            Gln His Gly Gln Pro Leu Gly Lys Phe Leu Gln Asp Ile Leu Trp Glu
                 35                  40                  45

Glu Val Asn Glu Ala Pro Ala Asp Lys
                 50                  55

<210> SEQ ID NO 11
<211> LENGTH: 447
<212> TYPE: DNA
<213> ORGANISM: Porcine

<400> SEQUENCE: 11
agctgaggcc atgccctcca cggggaccat ttgcagcctg ctgctcctca gcgtgctcct      60
catggcagac ttggccatgg cgggctccag cttcttgagc cccgaacacc agaaagtgca    120
ggtaagacgt ctccccagag ccccggcttc tggcgggtac ctcatcccag cccttccatg    180
agttgggacc tgggctcacc tgctctgggc ttcaggcctc tcccaaggag gactctggat    240
ctgcaaggga gcccatacct tgctctgctt ctggaaggaa gtagtgggg tgggtgggca     300 tcttagggcc tcaagagagc agttcctctt ccagcagag aaaggagtcc aagaagccag     360
cagccaaact gaagccccgg gccctggaag gctggctcgg cccagaagac agtggtgagg    420
tggaaggcac ggaggacaag ctggaaa                                       447

<210> SEQ ID NO 12
<211> LENGTH: 1095
<212> TYPE: DNA
<213> ORGANISM: Porcine
<220> FEATURE:
<221> NAME/KEY: misc_feature
<222> LOCATION: (530)..(530)
<223> OTHER INFORMATION: N is not determined
<220> FEATURE:
<221> NAME/KEY: misc_feature
<222> LOCATION: (574)..(803)
<223> OTHER INFORMATION: N is not determined
<220> FEATURE:
<221> NAME/KEY: misc_feature
<222> LOCATION: (1076)..(1076)
<223> OTHER INFORMATION: N is not determined

<400> SEQUENCE: 12
tcagtccgac cagcacggcc agccctgggg gaaatttctc caggacatcc tctgggaaga     60
ggtcaatggt aagtccccgt cccggctaag gtcaattcca agttcctggg agtcccagtg    120
tgagcccatc tatgggtaac aaaacagaaa tttccttccc catccctgcc tctctaaaga    180
gcttctgtgg ccttctgtgg cacaggatcc aatgttgtta ctatagagtt ttgggtcact    240
gcagtggtgt gggcctggga agttccacat gctgcaagta cagccaaaaa ataaaaaagg    300
gcctttaatt gctctttccc gggagttccc gttgtggctc agcagttagc gaatctgact    360
agcatccatg aggatgcagg ttcgatccct ggccttactc agtgggttaa agatctggca    420
ttgccgtgaa ctgtggtgta gttgcagaca cggctcagat cctgcattgc tgtgtctgtg    480
gtgtaggccg gtagctacag ctccgatttg accctaacc tgggaacctn cttatgctgc    540
aagtgctgcc ctgaaaaaga aaaaaaaaa ctgnnnnnnn nnnnnnnnn nnnnnnnnnn        600 nnnnnnnnnn nnnnnnnnnn nnnnnnnnnn nnnnnnnnnn nnnnnnnnnn nnnnnnnnnn    660
nnnnnnnnnn nnnnnnnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnnnnnnnn nnnttttttt tttttttccc ctttttttttt ttttttttg    840 gccatgcgtg cagcatgcca atgttcctag gccagggaac ccaagccaca gcagtgacaa    900
```

```
ccctggatcc ttaaggaact aggccaccag ggaactccag aaaagccatc tctgatggca        960
atggcagaac agcacagaat tttgacttga tctcttgctt ttcagaggcc ccggccgaca       1020
agtgattgtc cctgagacca gccacctctg ttctcccagc ctcctaaggg ctcacntggc       1080
ttacagtacg cttcc                                                        1095
```

```
<210> SEQ ID NO 13
<211> LENGTH: 19
<212> TYPE: DNA
<213> ORGANISM: Artificial
<220> FEATURE:
<221> NAME/KEY: misc_feature
<223> OTHER INFORMATION: Forward Primer

<400> SEQUENCE: 13
caggaagacc agctgaggc                                                      19

<210> SEQ ID NO 14
<211> LENGTH: 20
<212> TYPE: DNA
<213> ORGANISM: Artificial
<220> FEATURE:
<221> NAME/KEY: misc_feature
<223> OTHER INFORMATION: Reverse Primer

<400> SEQUENCE: 14
gaaccggatt tccagcttgt                                                     20

<210> SEQ ID NO 15
<211> LENGTH: 20
<212> TYPE: DNA
<213> ORGANISM: Artificial
<220> FEATURE:
<221> NAME/KEY: misc_feature
<223> OTHER INFORMATION: Forward Primer

<400> SEQUENCE: 15
gttgggatca agttgtcagg                                                     20

<210> SEQ ID NO 16
<211> LENGTH: 20
<212> TYPE: DNA
<213> ORGANISM: Artificial
<220> FEATURE:
<221> NAME/KEY: misc_feature
<223> OTHER INFORMATION: Reverse Primer

<400> SEQUENCE: 16
cctcagagct gggtgtgata                                                     20
```